US005215903A

United States Patent [19]

Paszkowski et al.

[11] Patent Number: 5,215,903

[45] Date of Patent: Jun. 1, 1993

[54] PROCESS FOR THE MAINTENANCE AND PROLIFERATION OF DEFECTIVE NON-INFECTIOUS VIRUS GENOMES IN PROLIFERATING PLANT MATERIALS

[75] Inventors: Jerzy Paszkowski, Herrliberg, Switzerland; Gabor Lazar, Belmont, Mass.; Hideaki Shinshi, Tsuchiura, Japan; Isabelle Rauseo, Morschwiller-les-Bas, France; Thomas Hohn, Arlesheim; Ingo Potrykus, Magden, both of Switzerland

[73] Assignee: Ciba-Geigy Corporation, Ardsley, N.Y.

[21] Appl. No.: 884,328

[22] Filed: May 11, 1992

Related U.S. Application Data

[63] Continuation-in-part of Ser. No. 465,512, Jan. 16, 1990, abandoned, which is a continuation-in-part of Ser. No. 074,593, Jul. 19, 1987, abandoned, which is a continuation-in-part of Ser. No. 636,946, Aug. 2, 1984, abandoned.

[30] Foreign Application Priority Data

Aug. 4, 1983 [CH] Switzerland ........................ 4235/83

[51] Int. Cl.[5] ........................ C12N 15/00; C12N 7/00; C12N 7/04; C12N 5/00; C12N 5/02; A01H 1/04

[52] U.S. Cl. .............................. 435/172.3; 435/172.1; 435/235.1; 435/236; 435/240.4; 435/240.47; 435/240.54; 800/205; 935/25; 935/57; 935/67

[58] Field of Search ............... 435/172.1, 172.3, 235.1, 435/236, 240.4, 240.47, 240.54, 320.1; 800/205; 935/25, 35, 57, 67

[56] References Cited

U.S. PATENT DOCUMENTS

| | | | |
|---|---|---|---|
| 4,407,956 | 10/1983 | Howell | 435/172.3 |
| 4,536,475 | 8/1985 | Anderson | 435/172.3 |

FOREIGN PATENT DOCUMENTS

| | | | |
|---|---|---|---|
| 0570954 | 4/1984 | Australia . | |
| 0022434 | 1/1981 | European Pat. Off. | 435/172.3 |
| 0067553 | 12/1982 | European Pat. Off. | 435/172.3 |
| 0095805 | 12/1983 | European Pat. Off. | 307/268 |
| 0164575 | 12/1985 | European Pat. Off. | 435/172.3 |
| 2326944 | 5/1973 | Fed. Rep. of Germany | 435/172.3 |
| WO8402919 | 8/1984 | PCT Int'l Appl. | 435/172.3 |

OTHER PUBLICATIONS

Ohgawara et al. 1983. Protoplasma 116:140–148.
Goodman et al. 1987. Science 236:48–54.
Biological Abstracts, 67, 1979, Ref. No. 56,745.
Chemical Abstracts, 89, 1978, p. 286, Ref. No. 56,249t.
Nature, 294, No. 5843, 1981/1982, pp. 773–776, (Gronenborn et al.).
Chemical Abstracts, 100, 1984, p. 264, Ref. No. 19990c.
Chemical Abstracts, 94, 1981, p. 412, Ref No. 62,040n.
Nature, 293, 1981, pp. 483–486, (Howell et al.).
Nature, 293, No. 5830, 1981, pp. 265–270, (Cocking et al.).
Chemical Abstracts, 98, 19823, p. 132, Ref. No. 66,277a.
Biological Abstracts, 77, No. 8, 1984, Ref. No. 62,639.
Mol. Gen. Genet., 183, 1981, pp. 209–213, (Otten et al.).
Basic Life Sci., 26, 1983, pp. 121–142, (Gardner).

(List continued on next page.)

*Primary Examiner*—David T. Fox
*Attorney, Agent, or Firm*—Steven R. Lazar; JoAnn Villamizar

[57] ABSTRACT

A process for the maintenance and proliferation of defective, non-infectious viruses or virus genomes, comprising mutations, i.e. deletions, substitutions, insertions and new rearrangements of the viral genes or combinations of the virus DNA with heterologous genetic material in proliferating plant material and for the regeneration of whole plants containing stably integrated into their genome said defective, non-infectious virus DNA.

10 Claims, 1 Drawing Sheet

OTHER PUBLICATIONS

Hildebrandt 1977 "Single Cell Culture, Protoplasts and Plant Viruses" in Plant Cell Tissue and Organ Culture, Springer-Verlag. pp. 581-646.
Langenham et al., 1977 "Desease-free plants via tissue culture propagation" Hort Sci., vol. 12(2), pp. 149-150.
Wu et al., 1960, Phytophathology 50, pp. 587-594.
Shillito et al., 1983, Plant Cell Reports 2, pp. 244-247.
Bhojwani et al., *Plant Tissue Culture, Theory and Practice,* Elsevier, 1983, pp. 306-307.
Thorpe, *Plant Tissue Culture-Methods and Applications in Agriculture,* Academic Press, 1981, p. 91.
Lesney et al., *J. Gen. Virol,* 57:387-395 (1981).
Kubo et al., *J. Gen. Virol.,* 27:293-304 (1975).
Kikkawa et al., *J. Gen. Virol.,* 63:451-456 (1982).
Furusawa et al., *J. Gen. Virol.,* 48:431-435 (1980).
Aoki et al, 1969, Virology 39, pp. 439-448.
Hildebrandt, 1958, PNAS 44, pp. 354-2363

PROCESS FOR THE MAINTENANCE AND PROLIFERATION OF DEFECTIVE NON-INFECTIOUS VIRUS GENOMES IN PROLIFERATING PLANT MATERIALS

This application is a continuation-in-part of application Ser. No. 465,512, filed Jan. 16, 1990, now abandoned, which is a continuation-in-part of application Ser. No. 07/074,593, filed Jul. 17, 1987, now abandoned, which is a continuation-in-part of application Ser. No. 06/636,946, filed Aug. 2, 1984, now abandoned.

FIELD OF THE INVENTION

The present invention relates to a process for the maintenance and proliferation of defective, non-infectious viruses or virus genomes, comprising mutations, i.e. deletions, substitutions, insertions and new rearrangements of the viral genes or combinations of the virus DNA with heterologous genetic material, in proliferating plant material and to a process for the regeneration of whole plants containing stably integrated into their genome said defective, non-infectious virus DNA.

Plant material with novel or improved properties can be produced by using genetically manipulated viruses as vectors when inserting new genetic information into plant hereditary material.

Owing to the rapid increase in world population, the genetic modification of useful plants is a major point of focus of biological research. On the one hand there is the search for alternative reproducible sources of food, energy and raw materials, e.g. new plant species, especially hybrid species with valuable properties such as increased resistance to pathogens (e.g. phytopathogenic insects, fungi, bacteria, viruses etc.), to herbicides, insecticides or other biocides, to atmospheric influences or location conditions (e.g. heat, cold, wind, soil condition, moisture, dryness etc.), or with increased formation of reserve or storage substances in leaves, seeds, tubers, roots, stalks etc. On the other hand, in addition to the growing need for valuable biomass, there is also an increased need for pharmaceutically acceptable active ingredients of plant origin and derivatives thereof, e.g. alkaloids, steroids and the like, which, because of the low yield from natural sources, are being increasingly made available by alternative methods, for example by extraction from genetically manipulated plant species.

Accordingly, there is growing interest in the practical possibility of selectively manipulating numerous plant species.

One means of attaining this object is the transfer of foreign genes to isolated plant cells, the replication and expression of the genetic material, as well as its propagation and maintenance in all daughter cells formed by cell division from the initial cell. Such daughter cells may exist in the form of single cells, tissue cultures or whole plants.

Dividing plant cells have a tendency to block the infiltration of viruses and to inhibit, partially or completely, the viability and multiplication capacity of viruses.

For example, it is known that cauliflower mosaic virus (CaMV) is able to proliferate in the differentiated cells of a plant and to infect all other differentiated cells, but the growth centres or meristems, i.e. the dividing cells, are not infected. Thus virus-free plants can be regenerated from virus-infected plants through a meristem culture.

Additionally it has been supposed that for the transformation of hereditary plant material using viruses as vectors, and for the production of genetically identical progeny of the initial plant material, it is necessary to cultivate viruses without loss of their ability to self-replicate and infiltrate new host cells.

It was therefore to be expected that the use of viruses as vectors for the transfer of new genetic information in many cases would not lead to genetically transformed plant material, as the viruses either do not infiltrate proliferating plant material or would die therein, or genetic material which is inserted into proliferating plant cells through plant viruses would not be absorbed into the hereditary material of the plant cells or would not replicate. According to Kriedel and Goodman [J. C. Kriedel and R. M. Goodman, BioEssays Vol. 4(1), pp. 4–8, (1986)], for example, ". . . caulimoviruses do not integrate into the chromosomal DNA of their host".

Within the scope of the present invention this prejudice could be overcome.

Prior to the present invention, in constructing a vector-system for the transformation of plants it was necessary to make a choice between a viral vector and an integration-type vector such as the ti-plasmid specifically, the T-DNA border regions of the Ti-plasmid.

A viral vector could only be used for a systemic infection of the host plant whereupon an integration type vector delivers its foreign genetic material into the plant chromosome and, therefore, is also only useful in dividing plant material. [R. E. Gardner, Plant Viral Vectors: CaMV as an Experimental Tool, (pp. 123–124, viral versus integration vectors) in: Genetic Engineering of Plants, Kosue et al., ed. Plenum Press p.p. 121–127 (1982)]. Now by use of the present invention the possibility opens up to utilize plant viruses, particularly plant viruses without the T-DNA border regions of the Ti-plasmid as integration-type vectors too.

Surprisingly, it has been found that it is possible to cultivate defective, non-infectious viruses or defective, non-infections virus genomes without the T-DNA border regions of the Ti-plasmid comprising mutations, i.e. deletions, substitutions, insertions and new rearrangements of the viral genes and combinations of the virus DNA with heterologous genetic material in dividing, i.e. proliferating, plant material and to insert said virus genomes into plant genomes.

By carrying out the process of the present invention it is now possible to cultivate defective, non-infectious virus genomes in dividing, i.e. proliferating plant material (protoplasts, cells or tissues) and stably maintain and proliferate the mutant viral genome therein (see example 5). It has been found that the viral DNA is integrated into and stably maintained in the plant genome. The present invention therefore opens up a lot of new possibilities to manipulate plant material.

So far it was only possible to integrate very small genes or gene fragments (up to 500 base pairs) into the viral genome, for example of CaMV, because there are only a few sites around the viral genome, which are not essential for infectivity and which are therefore suitable for the exchange with foreign DNA material. Thus, by carrying out the process of the present invention, it is possible to integrate normally sized genes (up to 1200 base pairs, like the kanamycin-resistance gene) into the deletion site of the defective viral genome, transform plant protoplasts, cells or tissues and stably maintain and proliferate the foreign genetic material together with the mutant viral genome in proliferating plant material.

There are substantially no limitations with respect to the extent of the inserted genetic information and plants, which contain such defective viruses or their genomes exhibit no symptoms of disease.

SUMMARY OF THE INVENTION

Accordingly, the present invention relates to a process for the maintenance and proliferation of defective, non-infectious virus genomes comprising mutations, i.e. deletions, substitutions, insertions and new rearrangements of the viral genes and combinations of the virus DNA with heterologous genetic material in proliferating plant material, which process comprises cultivating isolated plant protoplasts, cells or tissues which contain said virus genomes without the T-DNA border regions of the Ti-plasmid in a suitable culture medium. The process of this invention also encompasses the cultivation and regeneration of whole plants. Some of the plants so obtained are resistant to further virus infections (cross-resistance).

It has been known for a long time, that inoculation of plants with mild strains of viruses or viroids prevents more virulent strains of the same or related virus strains from infecting said plants and causing more severe disease symptoms.

This phenomenon, referred to as "cross-protection" and first discovered by McKinney (1929) with tobacco mosaic virus (TMV), has been used to protect certain crop plants such as tomatoes, potatoes and citrus against attack of tomato mosaic virus, potato spindle tuber viroid and citrus tristeza virus, respectively in order to reduce yield losses [Brodbent, L., 1976; Fernow, K. H., 1967; Costa, A. S. and Muller, G. W., 1980].

Nevertheless infection of healthy crop plants with mild strains of pathogenic viruses to confer "cross-resistance" to said plants, contains many risks, particularly the possibility of causing an epidemic disease, provided, for example, the used mild virus strain has mutated into a virulent form.

Within the scope of the present invention it is now possible to confer "cross-resistance" to plants without previously infecting them using wild virus variants of pathogenic strains, avoiding the risk of causing a disease outbreak.

In one embodiment of this invention plants are regenerated from plant protoplasts, cells or tissues containing integrated into their genome defective non-infectious viral DNA or DNA fragments, said viral DNA or DNA fragments conferring "cross-resistance" to the regenerated plant.

Within the scope of this invention it is therefore possible to use non-infectious viruses which are not viable under natural conditions, particularly non-infectious viruses without the T-DNA border regions of the Ti-plasmid, (defective viruses) and have substantially no limitation with respec to the extent of the inserted genetic information, or the genomes thereof, such that the plants which contain such viruses or their genomes exhibit no symptoms of disease. Hence defective viruses can be used with particular advantage as vectors for genetic information. Further, it is possible to regenerate whole plants, which are resistant to pathogenic viruses, from protoplasts, cells or tissues which contain defective viruses or their genomes.

Within the scope of this invention, some terms commonly used in recombinant DNA and plant genetics technology are utilized.

In order to provide a clear and consistent understanding of the specification and claims, including the scope given such terms, the following definitions are provided:

Virus Genomes: genetic information of a virus in the form of original DNA
original RNA
a transcript
cDNA Defective, non-infectious Viruses or defective non-infectious Virus Genomes:

viruses or virus genomes which are not viable under natural conditions and which have lost their ability to replicate in plant material and, therefore, to infect their host plants systemically on account of deletions, mutations, new combinations or combinations with new genetic material. The foregoing is inclusive of viruses or viruses genomes without the T-DNA border regions of the Ti-plasmid.

Plant Promoter: A DNA expression control sequence that is capable of causing the transcription in a plant of any homologous or heterologous DNA genetic sequence operably linked to such promoter.

Plant: Any photosynthetic member of the kingdom Planta that is characterized by a membrane-bound nucleus, genetic material organized into chromosomes, membrane-bound cytoplasmic organelles, and the ability to undergo meiosis.

Plant Cell: The structural and physiological unit of plants, consisting of a protoplast and cell wall.

Plant Tissue: A group of plant cells organized into a structural and functional unit.

Plant Organ: A distinct and visibly differentiated part of a plant such as root, stem, leaf or embryo.

Protoplast: isolated plant cell without cell walls, having the potency for regeneration into a cell culture or a whole plant Cell Culture: proliferating mass of cells in a undifferentiated state.

Figure 1:
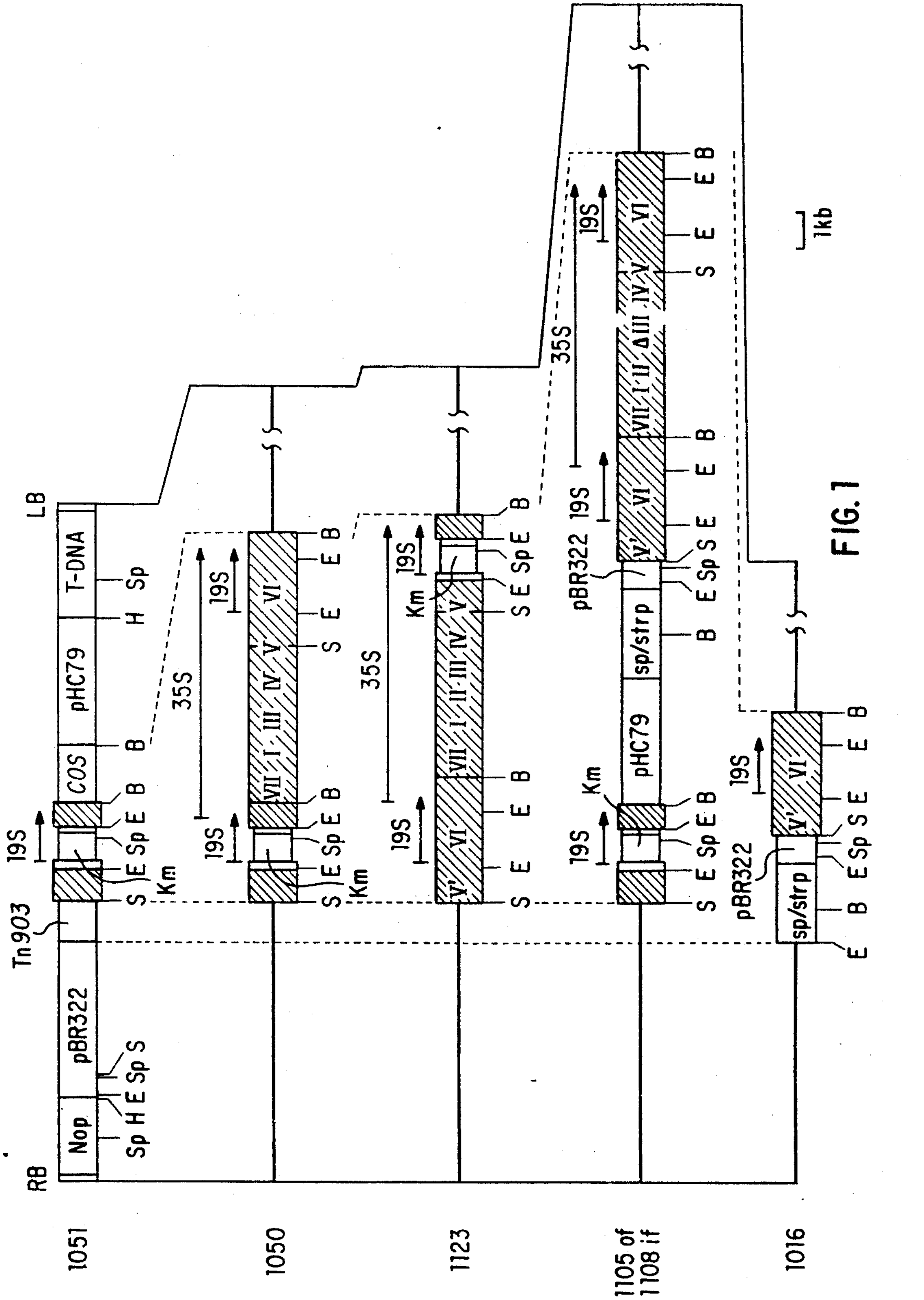
FIG. 1: Constructs used for transformation
Restriction sites.

B=BstEII, E=EcoRV, H=HindIII, S=SalI, Sp=SphI.

1051: Control construct containing the Km gene.

1050: 1.1 mer genome of wild type CaMV-DNA [a hybrid of strains 4-184 (genes VII-V) and S (Gene VI)]. This construct allows for transcription of genomic RNA. Inoculated turnips show vein clearing symptoms on the leaves (FIG. 6A).

1123: 1.1 mer genome of wild type CaMV-DNA [a hybrid of strains DH (genes VII-V) and S (gene VI)], which needs to recombine in order to build viable virus. This construct induced strong stunting of inoculated turnips and the leaves of infected plants turned pale green with mosaic or mottle type symptoms (FIG. 6A).

1108: 1.3 mer genome of CaMV (strain S) with an in frame deletion within gene III.

1105: 1.3 mer genome of CaMV (strain S) with an out of frame deletion within gene III.

1016: CaMV gene VI construct. CaMV strain S DNA. Agroinfection with strains 1108, 1105 and 1016 did not result in symptom formation on turnip plants.

LB/RB: Left, respectively, right border of the Ti-plasmid.

Nop: Nopaline synthase gene; located in the T-DNA of *A. tumefaciens* (nopaline strains).

pBR322: Complete sequences cut at HindIII site. Replace the oncogenic functions in Ti plasmid pGV3850 (Zambryski et al., 1983).

pHC79: Sequences from BstEII to HindIII.

cos: Cosmid sequences from phage lambda. Tn903: Kanamycin phosphotransferase gene of transposon Tn 903.

Km: aminoglycoside phosphotransferase II gene from transposon Tn5. The SalI-BstEII fragment, containing the Km gene is derived from pCaMV6km (Paszkowski et al., 1986).

I-VII: CaMV genes (boxes with dotted pattern).

19S/35S: Transcripts starting at the 19S or at the 35S promoter.

DETAILED DESCRIPTION OF THE INVENTION

Suitable initial plant materials for the process of the invention are in particular isolated protoplasts, preferably those of agriculturally cultivated plants. Suitable cultivated plants in this context are in particular those of the families Gramineae, Solanaceae, Compositae and Cruciferae and of the order Leguminosae.

Representatives of the aforementioned group are e.g. for Gramineae: wheat, rye, barley, oats, rice, maize, sorghum and sugar cane; for Solanaceae: potatoes, tomatoes and tobacco; for compositae: sun flowers, lettuce (*Lactuca sativa*), endive (*Cichorium endivia*) and camomile (Matricaria); for Cruciferae: various cabbage and beet varieties and oil and spice plants; and for Leguminosae: soybeans, lupins, lucernes, peas, beans and groundnuts.

Among the Cruciferae the genus Brassica, comprising e.g. rape, turnip, black mustard, white mustard, and cabbage and beet varieties, is to be singled out for special mention, in particular *Brassica rapa*, for example *Brassica rapa cv Just Right* and *Brassica napus*. A preferred embodiment of the process of the invention comprises culturing isolated plant protoplasts, cells or tissues which contain genomes of defective, non infective plant viruses.

According to another preferred embodiment of the process of this invention, the isolated plant protoplasts, cells or tissues contain defective, non-infectious virus genomes, which contain genetic material that is inserted into the plant genome of said protoplasts, cells or tissues. The viruses are in particular DNA viruses, preferably caulimoviruses, with cauliflower mosaic virus being most preferred.

Virus genomes which merit attention are primary viral DNA and DNA copies of viral RNA. The virus genomes can be genetically manipulated. For example, they can be restricted in their infectivity and their pathogenicity or contain inserted, foreign genetic material.

Genes which may be used in this invention may be homologous or heterologous to the plant cell or plant being transformed. It is necessary, however, that the genetic sequence coding for (a) desired proteinaceous product(s) be expressed, and produces a functional enzyme or polypeptide in the resulting plant cell. Thus, the invention comprises plants containing either homologous genes or heterologous genes that express desired proteinaceous product(s). Further, the heterologous gene(s) may be from other plant species, or from organisms of different kingdoms, such as microbs or mammals or they may be of synthetic origin.

In general it is expedient to culture isolated plant protoplasts, cells and tissues which contain virus genomes with inserted foreign genetic material of plant origin, preferably material of a plant whose genome differs from that of the genome of those protoplasts, cells or tissues which contain the virus genomes, i.e. that genetically different plants act as recipients and donors of the genetic material.

Primarily, gene(s) or genetic material are contemplated in this invention, which provide the transformed plant protoplasts, cells or tissues with valuable properties, such as increased resistance to pathogens (e.g. phytopathogenic insects, fungi, bacteria, viruses etc.), to herbicides, insecticides or other biocides, to atmospheric influences or location conditions (e.g. heat, cold, wind, soil condition, moisture, dryness etc.), or with increased formation of reserve or storage substances in leaves, seeds, tubers, roots, stalks etc.

Also included in the present invention are genes coding for pharmaceutically acceptable active ingredients, e.g. alkaloids, steroids, hormones and other physiologically active substances.

Therefore genes, which are contemplated in this invention include, but are not limited to, plant specific genes, such as the zeine gene [Wienand, U., et al., *Mol. Gen. Genet*, 182: 440–444 (1981)] mammalian specific genes, such as the insulin gene, the somatostatine gene, the interleucine gens the t-PA-genes [P-Pennica. et al., Nature 301, 214 (1983)] etc., or genes of microbial origin, such as the NPT II gene as well as gene of synthetic origin such as the insulin gene [Stephien, P., et al., Gene, 24: 281–297 (1983)] and the somatostatin gene [K. Itakura et al., *J. Am. Chem. Soc*, 97: 7327 (1975)].

At present some 300 plant viruses are known, which are divided into 25 different groups.

Viruses which can be used in this invention as vectors for the introduction of chimaeric genes into plant material are those which are suitable on account of their biological properties i.e. their host range, their virulence, their ease of mechanical transmission, their rate of seed transmission etc. and whose genetic material can be manipulated and reintroduced into the plant in a biologically active form, i.e., the DNA clones of said viruses must be infectious.

Viruses which are contemplated in this invention include, but are not limited to, members of the cauliflower group, including cauliflower mosaic virus (CaMV), and members of the geminiviruses whose genome is ssDNA including bean golden mosaic virus (BGMV), chloris striate mosaic virus (CSMV), cassava latent virus (CLV), curly top virus (CTV), maize streak virus (MSV) and wheat dwarf virus (WDV).

Also included in the present invention are RNA-containing plant viruses, which are able to be manipulated genetically using cDNA copies of their RNA genome.

Suitable carriers for the inserted foreign genetic material are in particular DNA viruses, preferably caulimoviruses, and of these most preferably cauliflower mosaic virus.

A particularly preferred embodiment of the process of the invention comprises culturing isolated plant protoplasts, cells or tissues of *Brassica rapa*, for example

*Brassica rapa cv Just Right*, which contain genomes of cauliflower mosaic virus with inserted foreign genetic material of a plant whose genome is different from the genome of the protoplasts, cells or tissues of Brassica rapa.

The introduction of defective, non-infectious virus DNA, more specifically, defective, non-infectious virus DNA without the T-DNA border regions of the Ti-plasmid, into plant protoplasts and the culturing of the isolated plant protoplasts, cells or tissues containing said virus DNA can be carried out by known methods or by methods analogous to known ones.

Isolated plant protoplasts which constitute suitable starting material for isolated cells and tissues can be obtained from any parts of the plant, for example from leaves, stems, blossoms, roots, pollen, cotyledons, seedlings or seeds. It is preferred to use leaf protoplasts. The isolated protoplasts can also be obtained from cell cultures. Methods of isolating protoplasts may be found for example in Gamborg, O. L. and Wetter, L. R., Plant Tissue Culture Methods, 1975, 11-21.

The working up and culturing of the plant material is conveniently performed in accordance with the following particulars, but without implying any restriction thereto.

The plant organs—provided the starting material does not consist of already sterile cell cultures—must be sterilised, for example by treatment with ethanol, $HgCl_2$, $Ca(OCl)_2$, or a commercial bleaching agent, and then washed carefully in sterile water. All subsequent manipulations must be carried out under absolutely sterile conditions. Sterility is also a requirement for the equipment and solutions employed.

The degradation of the cell walls of tissue aggregates is effected enzymatically, for example by using cellulases, hemicellulases or pectinases which are commercially available as microbial culture filtrates and are used in the concentration range of 0.001 to 5% (throughout this specification percentages are by weight, unless otherwise indicated).

During isolation and subsequent culturing, the turgor pressure of the plant cells must be equalised by a higher osmotic pressure of the isolation medium and of the culture medium. This is done by using osmotically active substances such as mannitol, sorbitol, saccharose, glucose, $CaCl_2$ or other neutral salt ions, alone or in combination with one another and/or with simple culture media. The osmotic pressure of the isolation and culture media is conveniently in the range from about 200 to 1000 mOs/kg $H_2O$ (Os=molality=mole of osmotically active particles/kg of solvent).

The enzyme mixtures are normally adjusted to pH values in the range from 5.2 to 8.0, preferably to pH 5.4.

Incubation of the tissues, which are conveniently cut into fine sections (when using leaves, the epidermis can also be removed), is effected in general in the temperature range from 5° to 40° C., normally at 24° C. The incubation time depends on the concentration of the enzymes, the incubation temperature, the type of tissue and the state of differentiation of the tissue. The incubation time is normally from 20 minutes to several days.

After incubation, the protoplasts are isolated by passing the incubated material through a sieve with a mesh size between 25 and 280 μm to remove undigested tissue, and concentrated by centrifuging. The protoplasts sediment or float, subject to their own buoyant density and to the density of the incubation and wash solution. The sedimenting or floating protoplasts are washed repeatedly by resuspending and centrifuging them in osmotically stabilised wash media (e.g. solutions of sugar alcohols, sugars or neutral salts, alone or combination with one another and/or culture media; pH in the range from 5.4 to 6.5) and subsequently taken up in culture media. An important factor in the subsequent culturing is the population density of the protoplasts, i.e. the number of protoplasts per milliliter of culture medium. The population density is advantageously in the range from 1 to $1\times10^6$/ml, with the optimum range being from about $2\times10^4$/ml to $6\times10^4$/ml.

The methods of culturing can vary from culturing in a liquid culture medium as thin layer in petri dishes, through drops or suspending drops with volumes in the range from about 1 μl to 200 μl, to culturing in solidified culture media (agar, agarose), or in combinations of solidified and liquid culture media. Culturing can be carried out in petri dishes, multiliter plates, containers, Erlenmeyer flasks, microcapillaries or tissue culture flasks which may be of coated or uncoated plastic or of glass.

Culturing can be carried out normally in a temperature range from 7° to 42° C., preferably in the range from 24° to 27° C. The temperature can either be kept constant or varied sequentially.

The light conditions during culturing may vary from permanent darkness to permanent light in the range from 500 to 5000 lux and alternating periods of light-/darkness. Alternating sequences of light/darkness are preferred.

There is already available a wide range of culture media, which differ in individual components or groups of such components. However, the composition of all media is in accordance with the following principle: they contain a group of inorganic ions in the concentration range from about 10 mg/l to several hundred mg/l (so-called macroelements, e.g. nitrate, phosphate, sulfate, potassium, magnesium, iron), a further group of inorganic ions in maximum amounts of several mg/l (so-called microelements, e.g. cobalt, zinc, copper, manganese), and a number of vitamins (e.g. inositol, folic acid, thiamine), a source of carbon and energy such as sucrose or glucose, and growth regulators in the form of natural or synthetic phytohormones from the classes of auxins and cytokinins in the concentration range from 0.01 to 10 mg/l. The culture media are additionally osmotically stabilised by the addition of sugar alcohols (e.g. mannitol) or sugar (e.g. glucose) or salt ions (e.g. $CaCl_2$), and are adjusted to a pH value of 5.6 to 6.5.

A more detailed description of commonly employed culture media can be found e.g. in Koblitz, H., Methodische Aspekte der Zell- und Gewebezüchtung bei Gramineen unter besonderer Berücksichtigung der Getreide, Kulturpflanze XXII, 1974, 93-157.

The culturing and incubation conditions such as temperature of the culture medium and ambient temperature, humidity, light intensity and duration thereof, replenishment or regeneration of culture media or change in their composition, can be adapted to the respective conditions such as nature of the protoplasts, type of virus genomes, rate of growth and division of the plant material and/or of the virus genomes, amount of débris and other factors.

Culturing of the isolated plant protoplasts, cells or tissues is carried out in a suitable culture medium, normally in a solidified culture medium.

Agarose can be used with pre-eminent success as gelling agent. The content of agarose in the nutrient medium is normally from 0.4 to 4%.

Agarose is one of the constituents of agar. Commercially available agar consists mainly of a mixture of neutral agarose and ionic agaropectin with a large number of attached side groups. Commercial agarose is obtained from agar by conventional commercial methods. Usually a number of side chains remain intact and determine the physicochemical properties such as gel formation and melting and gelling temperature.

Agarose which melts and gels at low temperature is obtained e.g. by subsequently introducing hydroxyethyl groups into the agarose molecule. Agarose modified in this manner shall be referred to throughout this specification as LMT (low-melting) agarose.

Examples of suitable agarose preparations are the following types: Sea Plaque LMT®, LMP®, type VII®, HGT®, HGTP®, LE Standard LMT® or Sea-Prep®.

The protoplasts, cells or tissues containing the virus genomes or their derivatives can be inserted into the culture medium in various ways. For example, the procedure can be that protoplasts, cells or tissues containing the defective, non-infectious viruses or defective, non-infectious virus genomes are put into a liquid, warm culture medium which already contains the gelling agent and which solidifies upon cooling. However, it is more advantageous to add a further portion of the liquid culture medium with the gelling agent to a suspension of the protoplasts, cells or tissues containing the virus genomes or their derivatives in a liquid culture medium without gelling agent and, after thorough mixing, to allow the medium to solidify.

Particularly good results are obtained by surrounding the solidified culture medium containing the protoplasts, cells or tissues which contain the defective, non-infectious viruses or defective, non-infectious virus genomes with liquid culture medium. Thus, for example, the solidified culture medium, after it has been plated in the dishes and plates, e.g. petri dishes, which are also used for culturing bacteria or yeast cells, can be cut into "segments" after it has solidified and the segments transferred to a liquid culture medium, preferably a nutrient solution. The term "segment" in the context of this invention denotes a three-dimensional irregular or, preferably, regular structure, e.g. discs, spheres, cubes, prisms, cones and the like, having an average cross-section of 1 to about 100 mm, preferably 2 to 60 mm, and most preferably, 2 to 10 mm. The volume ratio of segments to liquid culture medium or nutrient solution is advantageously in the range from 1:20 to 1:100. It is advisable to agitate the liquid culture medium containing the segments, for example by shaking on a gyratory shaker. The segmentation of the solidified medium is usually effected immediately after the medium has set or within a period of 4 weeks, preferably of 0 to 8 days after the medium has set, depending on the protoplast type. The best time for petunia protoplasts is the 4th day, for tobacco and *crepis capillaris* the 3rd day, after plating. When plating *Brassica rapa* protoplasts, segmentation is most preferably effected immediately after gelation of the agarose.

Segments are prepared which are preferably homogeneous in size and form. They may have an irregular or, preferably, regular structure, e.g. cones, cubes, prisms, discs and spheres. The segments have in general an average diameter or cross-section of 2 to 100 mm, preferably from 2 to 10 mm. For further details reference is made to EP-A 129,668.

Within the scope of the process according to the invention, it is possible to use both protoplasts, cells and tissues already containing defective, non-infectious viruses or defective, non-infectious virus genomes before being isolated, or those which were still virus-free before their isolation and are later artificially provided with the defective, non-infectious viruses or defective, non-infectious virus genomes.

A variety of methods for the introduction of non-infectious DNA-viruses into plant material are known in the art. One of these methods comprises the use of lipid vesicles, so-called liposomes, to encapsulate the genetic material followed by the fusion of said liposomes with the plant protoplast and the release of the encapsulated genetic material into the protoplast cytoplasm. (Lurquin PF, 1979). A further approach comprises the microinjection of genetic material contained in the vector directly into the plant cells by use of micro-pipettes to mechanically transfer the recombinant DNA.

In an alternate embodiment of this invention the DNA may be transferred into plant protoplasts after previously having been complexed with either polycationic substances such as, for example, poly-L-ornithine (Davey et al., 1980) or calcium phosphate (Krens et al., 1982) and/or after treatment of the protoplasts with polyethylene glycol (Paszkowski et al., 1984).

In particular this method involves contacting the DNA probe, comprising the probe molecule as well as a carrier DNA, with plant protoplast in a suitable osmotically stabilized incubation medium, such as, for example, but not limited to, $K_3$-medium (Nagy JI and Maliga R, Z. Pflanzenphysiologie 78: 453–455, 1976; Shillito RD et al., Mutation Research 81: 165–175, 1981), containing polyethylene glycol with a molecular weight preferably between 1000 and 10000 g/Mol, more preferably between 3000 and 8000 g/Mol, and in a concentration range from 5% to 30% (w/v). The protoplasts and the DNA probe may be incubated for a period of 10 to 60 min, preferably for a period of about 30 min.

The incubation may be carried out in the light or, preferably, in the dark at a temperature between 18° C. and 32° C., preferably between 22° C. and 28° C.

The process of the present invention also encompasses the maintenance and proliferation of defective, non-infectious viruses or defective, non-infectious virus genomes, comprising mutations, i.e. deletions, substitutions or new rearrangements of the viral genes and combinations of the virus DNA with heterologous genetic material by culturing the isolated plant protoplasts, cells or tissues containing said viruses or virus genomes in a suitable culture medium. The virus mutants may be those which are not viable under natural conditions, in particular mutants of plant viruses.

Mutants, which are not viable under natural conditions and which are contemplated in this invention include, but are not limited to, those, which are produced by insertion deletion or substitution mutagenesis, resulting in destruction of distinct regions of the viral genome, which are essential for infectivity, pathogenicity, and viability of the virus.

Insertions of a 12 bp fragment, for example, which cause an insertion of 4 amino acids in the resulting protein product made in open reading frame (ORF) I, III, IV (coat protein gene) and V of the CaMV genome proved to be lethal [Gardner et al., 1982].

The protoplasts, cells or tissues can contain for example primary viral DNA of such virus mutants which are not viable under natural conditions, or can contain corresponding mutants of such DNA viruses, representative types of DNA viruses being in particular caulimoviruses, especially cauliflower mosaic virus.

Also falling within the scope of this invention are regenerated plant cells, plant tissues or whole plants which contain defective, non-infectious viruses or defective, non-infectious virus genomes, provided they have been produced from isolated plant protoplasts containing these virus genomes in particular from protoplasts of cultivated plants.

Suitable cultivated plants in this context are in particular those of the families Gramineae, Solanaceae, Compositae and Cruciferae and of the order Leguminosae. Plants of the family Cruciferae to be singled out for special mention are those of the genus Brassica, in the present context preferably *Brassica rapa*, for example *Brassica rapa cv Just Right.*

Viruses are in particular plant viruses.

The regenerated plant cells, plant tissues or whole plants can contain for example primary defective, non-infectious viral DNA or defective, non-infectious DNA viruses, especially caulimoviruses and, most particularly, cauliflower mosaic virus. Regenerated plant cells or tissues of *Brassica rapa* which contain cauliflower mosaic virus are to be particularly mentioned.

In addition, the regenerated plant cells or tissues can contain those defective, non-infectious virus genomes thereof which carry genetic material which is inserted into the genome of the plant cells or tissues; or they can contain genetically manipulated virus genomes, for example those which contain inserted foreign genetic material that preferably originates from a plant whose genome differs from that of the plant cells or tissues which contain the defective, non-infectious virus genomes. Genetic material that is contemplated in this invention includes, but is not limited to, genes, which confer valuable properties to the plant, for example increased resistance such as increased resistance to pathogens (e.g. phytopathogenic insects, fungi, bacteria, viruses etc.), to herbicides, insecticides or other biocides, to atmospheric influences or location conditions (e.g. heat, cold, wind, soil condition, moisture, dryness etc.), or with increased formation of reserve or storage substances in leaves, seeds, tubers, roots, stalks etc. Hence regenerated plant cells or tissues can contain for example genomes of cauliflower mosaic virus with inserted foreign genetic material, in particular material from a plant whose genome differs from that of the plant cells or tissues which contain cauliflower mosaic virus.

A plant which contains cauliflower mosaic virus is, in the context of this invention, in particular *Brassica rapa*, for example *Brassica rapa cv Just Right.*

The present invention also relates to regenerated plants which contain defective, non-infectious virus genomes and have been produced from protoplasts containing said virus genomes by culturing, including their progeny, which progeny may have been produced both by sexual or by vegetative propagation.

In another of its aspects, the invention relates to the use of agarose for producing and culturing plant cells or tissues which contain defective, non-infectious virus genomes from isolated plant protoplasts containing said virus genomes.

The invention relates further to the propagation of viral in vitro produced mutants. Such mutants are propagated by infecting isolated plant protoplasts with genetically manipulated viruses or virus genomes, and culturing the infected protoplasts in a suitable culture medium, preferably an agarose-solidified culture medium, followed by culturing in further suitable media until full differentiation to form a plant. Plant regeneration from cultural protoplasts is described in Evans, et al., "Protoplast Isolation and Culture," in *Handbook of Plant Cell Culture,* 1:124–176 (MacMillan Publishing Co. New York 1983); M.R. Davey; "Recent Developments in the Culture and Regeneration of Plant Protoplasts," *Protoplasts,* 1983-Lecture Proceedings, pp. 19–29, (Birkhauser, Basel 1983); P. J. Dale, "Protoplast Culture and Plant Regeneration of Cereals and Other Recalcitrant Crops," in *Protoplasts* 1983-Lecture Proceedings, pp. 31–41, (Birkhauser, Basel 1983).

A further object of the invention is the use in protoplast transformation systems of viral in vitro produced mutants, which have been propagated as described above using genetically manipulated viruses or virus genomes.

Virus production in cell cultures formed from protoplasts can be detected for example in two different ways: a) by hybridisation of the cell culture DNA with radioactively marked viral DNA or b) by reinfecting healthy plants with cell culture extracts.

Methods of isolating protoplasts and of detecting virus production are known. However, it is advisable to vary the methods in accordance with the respective conditions.

The production of isolated protoplasts will be described in more detail below, followed by Examples relating to protoplast and cell proliferation and to detecting virus production.

*Brassica rapa* plants (turnips) are reared in a greenhouse and, when in the 5-leaf stage, infected with cauliflower mosaic virus by one of the methods commonly employed in virology (rubbing virus suspensions into leaf surfaces by mechanical injury with carborundum powder). Systemically infected plants are transferred to a growth chamber for further culturing under the following conditions: 12/12 hours in light/darkness rhythm, 5000 lux light intensity (SILVANIA daylight fluorescent tubes), 27° C. day temperature and 20° C. night temperature, 70% constant relative humidity, twice daily treatment of the plants growing in pots in an earth/sand/turf mixture with 0.1% of a plant fertiliser concentrate, e.g. Greenzit ® fertiliser solution (CIBA-GEIGY AG, Basel). The protoplasts are routinely isolated from 12 cm long leaves of the systemically infected plants as follows: The leaves are washed with tap water, sterilised for 30 minutes in 0.5% calcium hypochloride solution and then carefully washed 5 times in sterile deionised water under sterile conditions on a sterile work bench. The leaf area is divided into 2 cm wide strips which are stacked and cut into 1 mm wide cross-sections with ultra-sharp razor blades. The leaf cross-sections are transferred to an osmotically stabilised enzyme solution of the following composition, with which they are vacuum-infiltrated: 1% cellulase ONOZUKA R10+0.1% pectinase MACEROZYME R10 (both supplied by Yakult Pharmaceutical Industry Co. Ltd., 8–21 Shingikan-cho, Nishinomiya, Japan), dissolved in a mixture of 0.45 molar mannitol (3 vol) and 0.17 molar $CaCl_2$ (1 vol), pH adjusted to 5.4 with 0.1 molar KOH. The osmotic pressure of the enzyme solution is about 510 mOs/kg $H_2O$. Most of the tissue is converted into isolated protoplasts by incubating the segments for 16 hours at 12° C. The protoplast suspension is filtered through a 100 μm steel sieve to remove debris, transferred to sterile centrifuge tubes and sedimented for 10 minutes at 75 g. The sedimented protoplasts are resuspended in sterile osmoticum (0.175 molar $CaCl_2$+0.5% MES buffer (MES=2-(N-morpholino)ethanesulfonic acid; sigma No. M-8250), adjusted to pH 5.7, 510 mOs/kg $H_2O$) and washed 3 times by sedimentation at about 500× g and resuspension in the osmoticum. The protoplasts are then resuspended in the culture medium described in Example 1 and adjusted to a population density of $8 \times 10^4$/ml.

The method used for protoplast transformation was as originally developed by Krens et al. (1984), with modifications according to Paszkowski J, et al. (1984) $2 \cdot 10^6$ protoplasts were used per transformation treatment, each of which contained a total of 50 μg of DNA (10 μg of the viral DNA and 30-40 μg of calf thymus DNA as carrier).

In particular this method involves contacting the DNA probe, comprising the probe molecule as well as a carrier DNA, with plant protoplast in a suitable osmotically stabilized incubation medium, such as, for example, but not limited to, $K_3$-medium (Nagy JI and Maliga R, Z. Pflanzenphysiologie 78: 453-455, 1976; Shillito RD et al., Mutation Research 81: 165-175, 1981), containing polyethylene glycol with a molecular weight preferably between 1000 and 10000 g/Mol, more preferably between 3000 and 8000 g/Mol, and in a concentration range from 5% to 30% (w/v). The protoplasts and the DNA probe may be incubated for a period of 10 to 60 min, preferably for a period of about 30 min.

The incubation may be carried out in the light or, preferably, in the dark at a temperature between 18° C. and 32° C., preferably between 22° C. and 28° C.

EXAMPLE 1

Culturing protoplasts of *Brassica rapa*

Culture medium
modified according to Kao, K.N. (1977), Mol. Gen. Genet. 150, 225-230, and Koblitz, K. and Koblitz, D. (1982), Plant Cell Reports 1, 147-150.

| | | | | | |
|---|---|---|---|---|---|
| $NH_4NO_3$ | 600 | mg/l | Na-pyruvate | 5 | mg/l |
| $KNO_3$ | 1900 | " | citrate | 10 | " |
| $CaCl_2.2H_2O$ | 600 | " | malate | 10 | " |
| $MgSO_4.7H_2O$ | 300 | " | fumarate | 10 | " |
| $KH_2PO_4$ | 170 | " | nicotinamide | 0.5 | " |
| KCl | 300 | " | pyridoxine-HCl | 0.5 | " |
| $FeCl_3.6H_2O$ | 27 | " | thiamine-HCl | 5.0 | " |
| $Na_2EDTA$ | 74.6 | " | D-calcium pantho-tenate | 0.5 | " |
| $MnSO_4.1H_2O$ | 10 | " | folate | 0.2 | " |
| $Na_2MoO_4.2H_2O$ | 0.25 | " | p-aminobenzoicacid | 0.01 | " |
| $H_3BO_3$ | 3.0 | " | biotin | 0.005 | " |
| $ZnSO_4.7H_2O$ | 2.0 | " | choline chloride | 0.5 | " |
| $CuSO_4.5H_2O$ | 0.025 | " | riboflavin | 0.1 | " |
| $CoCl_2.6H_2O$ | 0.025 | " | ascorbic acid | 1.0 | " |
| KI | 0.75 | " | Vitamin D3 | 0.005 | " |
| glucose | 68'400 | " | | | |
| sucrose | 125 | " | | | |
| fructose | 125 | " | Vitamin B12 | 0.01 | " |
| ribose | 125 | " | m-inositol | 100 | " |
| xylose | 125 | " | casein hydro-lysate | 125 | " |
| mannose | 125 | " | 2,4-dichlorophen-oxyacetic acid | 0.25 | " |
| rhamnose | 125 | " | α-naphthylacetic- | 0.5 | " |
| Nitsch, J. P. and Nitsch. C (1969), Science 163, 85-87. | | | | | |
| $KNO_3$ | 950 | mg/l | m-inositol | 100 | mg/l |
| $NH_4NO_3$ | 720 | " | nicotinic acid | 5 | " |
| $MgSO_4.7H_2O$ | 185 | " | pyridoxine-HCl | 0.5 | " |
| $CaCl_2.2H_2O$ | 220.5 | " | thiamine-HCl | 0.5 | " |
| $KH_2PO_4$ | 68 | " | folic acid | 0.5 | " |
| $FeCl_3.6H_2O$ | 27 | " | biotin | 0.05 | " |
| $Na_2EDTA$ | 74.6 | " | glycine | 2 | " |
| $MnSO_4.1H_2O$ | 17.25 | " | agar (Difco) | 9000 | " |
| $H_3BO_3$ | 10 | " | sucrose | 20000 | " |
| $ZnSO_4.7H_2O$ | 10 | " | coconut milk (Gibco) | 2.5 | " |
| $Na_2MoO_4.2H_2O$ | 0.25 | " | 2,4-dichlorophen-oxyacetic acid | 0.25 | " |
| $CuSO_4.5H_2O$ | 0.025 | " | α-naphthylacetic acid | 0.5 | " |
| | | | 6-benzylamino-purine | 0.1 | " |
| pH (KOH) 5.8; autoclaved for 20 min at 1 atom. | | | | | |

Culturing method
Cell colonies obtained in Example 1, which have attained a diameter of 1 mm and more, are transferred to the surface of the above described agar-solidified culture medium and further incubated at 24° C. in permanent darkness.

In more than 20 experiments, protoplasts obtained from non-infected *Brassica rapa* plants and from *Brassica rapa* plants infected with cauliflower mosaic virus were regenerated to cell cultures in the above described manner.

EXAMPLE 3

Detection of virus proliferation by hybridising the cell culture DNA with radioactively marked cauliflower mosaic virus DNA.

| Aqueous solutions for the DNA hybridisation: | |
|---|---|
| proteinase K (Merck 24568): | 0.1 mg/ml of proteinase K<br>0.1% sodium azide<br>0.1% sodium dodecyl sulfate (=SDS) |
| alkali solution: | 0.5M NaOH<br>1.5M NaCl |
| neutral salt solution: | 3M NaCl<br>0.5M tris(hydroxymethyl)aminomethane buffer (=tris-HCl-buffer), pH 7.0 |

Method a) individual cell colonies of Example 2 are each incubated in 1 ml of 2-methoxyethanol for 5 hours at room temperature;

b) the 2-methoxyethanol is carefully removed by suction and the cell colonies are frozen in liquid nitrogen;

c) the frozen cell colonies are homogenised to powder in Eppendorf tubes;

d) the powdered material is suspended in 200 μl of $H_2O$ and thoroughly mixed;

e) the samples are centrifuged for 2 minutes in an Eppendorf centrifuge;

f) the clear supernatant is used for the DNA hybridisation.

Hybridisation g) 50 μl portions of the supernatant [q.v. f) above] are put into the filter chambers of the BRL dot hybridisation system (Bethesda Research Laboratories BRL No. 1050 MM), the filter of which must be moistened beforehand, and a mild vacuum is applied (water jet vacuum);

h) 200 μl of water are added and the samples are filtered;

i) 150 μl of the above proteinase K solution are put into each chamber, and the system is packed in plastic film and incubated overnight;

j) the proteinase solution is removed with suction, replaced by 150 μl of the above alkali solution and the samples are incubated for a further 15 minutes;

k) the alkali solution is removed with suction and replaced by 150 μl of the above neutral solution and the samples are incubated for a further 15 minutes;

l) after removal of the neutral salt solution, the filters are washed twice for 5 minutes with 150 μl of sodium chloride/sodium citrate buffer (=SSC: 17.5 g of NaCl and 8.8 g of sodium citrate per liter of $H_2O$; pH adjusted to 7 with NaOH);

m) after removal of the SSC, the filters are heated for 2 hours at 80° C.; and n) subsequently hybridised with radio-active CaMV DNA;

o) radio-activity on the filters was visualised by exposure to a film;

p) extracts from cell cultures which have contained CaMV or CaMV DNA hybridise on the filter with the radio actively marked CaMV DNA and show up black on the processed film. From the presence or absence of black areas on the film corresponding to the individual chambers of the BRL hybrid dot system it is possible to detect which of the tested cell colonies contained CaMV or CaMV DNA.

EXAMPLE 4

Detection of virus proliferation by reinfection of healthy plants with cell culture extract a) Individual cell colonies of Example 2 are each incubated in 1 ml of 2-methoxyethanol for 5 hours at room temperature;

b) the 2-methoxyethanol is carefully removed with suction and the cell colonies are frozen in liquid nitrogen;

c) the frozen cell colonies are homogenised to powder in Eppendorf tubes;

d) each of the homogenised samples is suspended in 200 μl of $H_2O$ and thoroughly mixed;

e) the samples are centrifuged for 2 minutes in an Eppendorf centrifuge;

f) the clear supernatant is used for the reinfection assays.

Reinfection

The supernatant (q.v. f) above) is rubbed with carborundum, under strict sterile conditions, into the top side of leaves of healthy *Brassica rapa* plants. The plants are kept for 3 to 4 weeks free from the possibility of any further virus infection and then examined for the occurrence of virus symptoms (mosaic symptoms, leaf vein transparency). Control plants treated with carborundum are kept under the same conditions as the inoculated plants. The occurrence or absence of virus symptoms after rubbing supernatant into the leaves of healthy plants is proof of the presence or absence of viable CaMV particles in the cell culture from which the supernatant has been obtained.

The results of the above described test showed that large amounts of virus have been formed in about 5% of the cell cultures which were regenerated from protoplasts of virus-infected plants.

EXAMPLE 5

Use of non-infectious virus mutants as vectors for cell clones in plant tissues.

Sap samples taken from different callus clones of *Brassica rapa* containing CaMV DNA are rubbed into the top side of leaves of healthy *Brassica rapa* plants. The plants are kept for 3 to 4 weeks free from the possibility of any other virus infection and then examined for the occurrence of virus symptoms. 50% of the clones are infectious and the plants which have been treated with the sap of these clones exhibit the usual symptoms of a CaMV infection. The viral DNA of these plants has a restriction pattern which is identical with that of the viral DNA of the sap sample used for the infection.

30% of the clones are non-infectious and DNA analysis shows that the virus genome exhibits deletions.

Based on the observation, that wild type CaMV can replicate in *B. campestris var. rapa* cell clones derived from infected plants and that during viral propagation in tissue culture its plant infectivity can be lost (example 5), the following experiment (example 6), was carried out to prove that viral genomes, which are defective with respect to replication in plants due to deletions or gene replacement, can replicate in tissue culture.

EXAMPLE 6

Integration of genetically engineered CaMV genome into high molecular weight plant genomic DNA a) Construction of the plasmid pCaMV6Km The plasmid pBR 327 CaKm+ described by Paszkowski et al., (1984), is digested with restriction endonuclease EcoRV and the EcoRV restriction fragment containing the kanamycin-resistant gene (NPT II) is used to replace the EcoRV fragment of the plasmid pCa20-Bal I which fragment contains the gene VI of cauliflower mosaic virus, yielding the plasmid pCaMV6km. The plasmid pCa20Bal 1 is a chimaeric CaMV plasmid which is derived from the natural deletion mutant CM4-184 [Brisson, N. et al. (1984)]. The entire region II is missing from this plasmid, except for the first 5 codons and the translation stop signal TGA. An XhoI coupling component is inserted immediately before the stop codon in region II. All manipulations are carried out as described by Maniatis et al. (1982).

b) Protoplast transformation and culture

The method used for protoplast transformation was as originally developed by Krens et al. (1982), with modifications according to Paszkowski J, et al. (1984). 1 ml aliquots of $2\cdot10^6$ protoplasts are used per transformation treatment, each of which are incubated for 30 min at room temperature in $K_3$ medium (Nagy and Maliga, 1976; 0.1 mg/l 2.4-D, 1 mg/l NAA, 0.2 mg/l BAP), containing 13% w/v PEG 6000 and a total of 50 μg of DNA (10 μg of each plasmid molecule digested with Sal 1 in order to release the viral DNA from the bacterial vector and 30–40 μg of calf thymus DNA as carrier). After transformation and washing of the DNA with F medium [Krens, F. A. et al., (1982); Krens, F. A. and Schilperoort, R. A., (1984)] with a pH of 5.3 (adjusted with KOH after autoclaving) the protoplasts are collected by sedimentation (5 min at 100 g) and resuspended in 30 ml of $K_3$-medium. Then the protoplasts are embedded in 1.5% agarose ($2.5\cdot10^5$ protoplasts/ml) in a modified KO medium [Liang-cai L, Kohlenbach W, (1982)] containing 0.5 mg/l NAA, 0.25 mg/l 2,4-D, 0.1 mg/l BAP, 520 mOs/kg$H_2O$ and cultured in an agarose bead type culture system [Shillito, R. D. et al., (1983)].

c) Selection of transformed cell clones

Selection is applied at day 4 of culture by the replacement of the culture medium surrounding the agarose beads with fresh medium containing antibiotic [50 mg/l kanamycin, Jimenez, A. and Davis, J. (1980)].

After three weeks of culture with replacement of the selective medium at 5 day intervals, the osmotic pressure of the culture medium is gradually reduced to 200 mOs/kg$H_2O$ by reducing the mannitol concentration. After 6 weeks visible resistant clones are picked up individually and are further cultured on 0.8% w/v agar-solidified KO-medium supplemented with 50 mg/l kanamycin sulphate.

DNA isolation from plant material and Southern blot analysis

The methods and conditions for DNA isolation and hybridisation are carried out as described previously [(EXAMPLE 3, Paszkowski J., et al. (1984)]

NPTII activity assay

NPTII activity is detected using the method described by Reiss et al. (1984) and adapted to plant material [Paszkowski J., et al. (1984)].

Infectivity and complementation test of engineered CaMV genome

CaMV DNA, amplified in *E. coli* by cloning on bacterial vector plasmids, is infectious on plants when cut out from the vector molecule and applied to wounded leaves [Howell, S. H. et al., (1980); Lebeurier, G. et al. (1980)]. *B. Campestris var. rapa* is used in infectivity tests and in protoplast transformation experiments.

Infectivity is determined by inoculation of young plants with Sal 1 restricted DNA of pCaMV6km or pCa20-Bal 1. DNA's are applied separately or as a 1:1 mixture. After 3 weeks, plants are examined for the development of CaMV specific mosaic symptoms. At the same time, DNA from inoculated leaves (site of infection) and from secondary infected leaves (infected by systemic spread) is examined by Southern blot hybridisation, Southern, E. M. (1975) in order to follow the fate of the applied DNA.

Application of pCaMV6km DNA alone never leads to the development of mosaic symptoms. Infection with pCa20-Bal 1 DNA, or with mixtures of both DNA's cause the mosaic symptoms typical of systemic infection by the wild-type virus.

Southern blot analysis, using specific probes which discriminate between the two DNA's applied, reveals that pCaMV6km is not able to spread systemically through the plant. This is also true in the case where pCaMV6km is applied together with pCa20-Bal 1 have never found pCa6km specific hybridisation signals in the secondary leaves of inoculated plants.

Transformation of isolated turnip mesophyll protoplasts and selection of antibiotic resistant cell lines In order to study the possibility of pCaMV6km replication at the cellular level in cultured plant cells turnip protoplast transformation experiments are undertaken.

Recently turnip mesophyll protoplast culture has been improved to c.a. 20% plating efficiency [Pisan, B. et al. (1983)], a level sufficient to approach DNA transformation. For protoplast transformation a modification of a DNA uptake procedure previously developed by Krens et al. (1982) is used. Readjustment of the pH of F medium [Krens et al., (1982)] to 5.5, which falls to 4.8 after autoclaving, is a prerequisite for survival of turnip protoplasts during the DNA treatment. Even so, recovery of protoplasts after transformation is not satisfactory in the majority of experiments. In only 4 out of 15 equivalent experiments was the plating efficiency at a level (10–15%) sufficient to carry out selection of transformants. Antibiotic resistant cell lines are recovered in 2 of these experiments.

We obtained 2 clones from kanamycin sulphate selection. These clones are grown further on agar-solidified media containing 50 mg/l kanamycin sulphate. As soon as the clones reached a size of approximately 1 g fresh weight of tissue, part of the material is subjected to Southern blot analysis and assayed for the presence of the NPTII gene product.

Form and arrangement of the foreign DNA in transformed kanamycin resistant cell lines DNA of the two clones selected and cultured on kanamycin-containing media (T12A and T12B) are analysed after 3, 6, 9 and 12 months of culture-the foreign DNA was stably maintained. When non restricted total cellular DNA is analysed, hybridisation with radioactively labelled pCaMV6km is detected only in the region of high molecular weight DNA greater than 50 kilobases in length. There is no detectable hybridisation in the region of 7.1 or 7.5 kb, the expected sizes for free copies of viral like molecules derived from plasmids pCaMV6km and pCa20-Bal 1, respectively. Further analysis of nuclear DNA confirmed the supposition that the major part of the Sal 1 fragment of pCaMV6km containing the hybrid viral genome had been integrated, generating junction fragments with plant DNA in both of the selected cell lines T12A and T12B. Reconstructions and mapping experiments suggested the presence of a single copy of the transforming DNA molecule per diploid genome of *B. campestris var. rapa*. The results of the Southern blot analyses suggest the following conclusions on the junctions of pCaMV6km DNA and plant DNA:

a) The 114 bp EcoRV fragment containing the hybrid marker gene is present in a non-rearranged form, which when correlated to tests for NPTII activity, can be taken as evidence for the integration of a functional copy of this gene into the plant genome.

b) EcoRV, BstEII and EcoRI restriction digests of nuclear DNA of T12A and T12B hybridised to probes specific for either the NPTII coding region or the 5′ and 3′ gene flanking sequences allowed for approximate mapping of the regions of the integrated pCaMV6km Sal 1 fragment. The fragments of foreign DNA integrated in two transformed lines are different and are probably integrated at different sites in the genome (as judged from the sizes of the border fragments). There are, however, also common features, in that both lines contain an unaltered (2297 bp long) EcoRI fragment of the linear molecule used for transformation and there is little rearrangement of the transforming DNA.

NPTII activity test of transformed cell lines

Kanamycin-specific phosphorylation, reflecting activity of NPTII, can be detected in crude plant protein extracts electrophoresed under non denaturing conditions in a 10% polyacrylamide gel.

Extracts of kanamycin resistant cell lines are tested for the presence of the NPTII activity.

Extracts of the kanamycin resistant cell lines (T12A and T12B) contain the expected NPTII specific activity, confirming the biological function of the integrated hybrid marker gene. Moreover the banding pattern of the enzyme is identical to that found in tobacco tissues expressing the enzyme from the same fused gene.

Analogous experiments have been carried out with plants of the species *Brassica napus* (rape).

The regeneration of *Brassica napus* protoplasts is achieved by use of a method described by Liang-cai Li and Kohlenbach, (1982).

EXAMPLE 7

Cross-protection in CaMV producing transgenic plants

Plants which are systemically infected with a virus are resistant to a secondary infection by a related virus strain. This phenomenon is called cross-protection but the exact mechanism is still unknown (Sherwood, *CIBA Foundation Sumposium,* 133:136–150 (1987)). In order to determine whether 1050- and 1123-transgenic plants exhibit cross-protection, these plants are superinfected by another CaMV strain. Transformed plants are inoculated with a CaMV strain, namely Ca-NB2, that has gene II replaced by a DHFR gene (dehydrofolate reductase gene) and thereby allowing distinction from virus produced by the transformed plants. Ca-NB2 has been constructed and tested for normal infectivity by Brisson et al., *Nature*, 310:511–514 (1984). Four 1123, four 1050 and two 1051 transformed (nopaline positive) plants are inoculated with extract of turnip leaves, systemically infected with Ca-NB2. Four weeks after the superinfection total DNA is extracted from the infected plants and from uninfected plants. The DNA is slot blotted to a Zeta probe membrane, hybridized with a $^{32}P$-labelled DHFR-specific probe and the membrane exposed to an x-ray film. The slot blot analysis shows that there is no replication of Ca-NB2 in 1050 transgenic plants and no or very little replication in 1123 transgenic plants which indicates that the plants are protected against secondary infection by Ca-NB2. The membrane is washed free of the DHFR-specific probe and then incubated with a CaMV-DNA-specific probe. The resulting autoradiogram shows that there is virus present in the superinfected transgenic plants. Progeny plants transgenic for the "recombination CaMV-construct" (1123) produce no infectious virus in cotyledons. Only in leaves that appear later, usually in the second leaf or sometimes much later, is infectious CaMV found, shown by slot blot analysis of total plant DNA or by infectivity tests on turnip plants. Progeny plants of 1050, however, produce infectious CaMV already in the cotyledons. This observation may be a reason for the slightly less complete cross-protection in 1123 plants compared to the 1050 plants. Another reason could have been the different CaMV strains used. The CaMV-DNA in construct 1050 consists mainly of strain 4-184 (gene VI of strain S) like the challenging virus (Ca-NB2), whereas construct 1123 consists of CaMV strain DH sequences.

The "cross-protection" observed in the above experiment can be attributed to recombination between Ca-NB2 and the virus produced by the transgenic plants to CaMV lacking the DHFR gene. Alternatively, the CaMV strains produced by the transgenic plants may replicate at a greater rate and thus out-compete the incoming Ca-NB2 virus. In order to test the ability of Ca-NB2 to compete in systemic spreading with strain DH (in construct 1123) or 4-184 (in construct 1050), leaf extract containing Ca-NB2 is inoculated with extract containing either of the other strains at the same time on turnip plants. The different virus extracts are either rubbed together on the same leaf or on separate leaves; once Ca-NB2 extract is inoculated on the younger leaf of a turnip and the 1050 extract on the following older leaf or vice versa. Isolation of total plant DNA and analysis by the slot blot technique using a DHFR-specific probe for DNA hybridization, shows that Ca-NB2 virus is present in high amounts. No differences are observed between the ways the double infections are performed.

REFERENCES

Brisson N, Paszkowski J, Penswick JR, Gronenbron B, Potrykus I, Hohn T: Expression of a bacterial gene in plants by using a viral vector *Nature* 310: 511–514, 1984.

Broadbent L, *Annu. Rev. Phytopathol.* 14: 75, 1976.

Costa A S and Muller G W, *Plant. Dis.* 64: 538, 1980.

Davey et al., *Pl. Sci. Lett.* 18: 307–313, 1980.

Fernow K H, *Phytopathology* 57: 1347, 1967.

Gamborg O L, Wetter L R., Plant Tissdue Culture Methods, 11–21, 1975.

Gardner R E: Plant Viral Vectors: CaMV as an Experimental Tool. In: Kosue et al. (eds), Genetic Engineering of Plants, Plenum Press, 121–127, 1982.

Howell S H, Walker L L, Dudley R K: Cloned cauliflower mosaic virus DNA infects turnips (*Brassica rapa*). *Sience* 208: 1265–1267, 1980.

Itakura K, et al., *J. Am. Chem. Soc.* 97: 7327, 1975.

Jimenez A, Davies J: Expression of a transposable antibiotic resistance element in Saccharomyces. *Nature* 287: 869–871, 1980.

Kao K N: *Mol. Gen. Genet.* 150: 225–230, 1977.

Koblitz H, Methodische Aspekte der Zell- und Gewebezüchtung bei Gramineen unter besonderer Berücksichtigung der Getreide, Kulturpflanzen XXII, 93–157, 1974

Koblitz K, Koblitz D, *Plant Cell Reports* 1: 147–150, 1982.

Krens F A, Molendijk L, Wullems G J, Schilperoort R A: In vitro transformation of plant protoplast with Tiplasmid DNA. *Nature* 296: 72–74, 1982.

Krens F A, Schilperoort R A: Ti-plasmid DNA uptake and Expression by protoplasts of *Nicotiana tabacum*. In: Vasil I K (ed) Cell Culture and Somatic Cell Genetics of Plants. Vol. 1, Laboratory Techniques. Academic Press, New York, 1984, p.p. 522–534.

Kriedel J C, Goodman R M, Bio Essays vol 4 (1): 4–8, 1986.

Lebeurier G, Hirth L, Hohn T, Hohn B: Infectivities of native and cloned DNA of cauliflower mosaic virus. *Gene* 12: 139–146, 1980.

Liang-cai L, Kohlenbach W: Somatic embryogenesis in quite a direct way in cultures of mesophyll protoplasts of *Brassica napus*. *Plant Cell Rep* 1: 209–211, 1982.

Lurquin P F, *Nucl. Acid. Res.* 6: 3773–3784, 1979.

Maniatis, Fritsch E F, Sambrook J: Molecular cloning. A laboratory manual. Cold Spring Harbor Laboratory, New York 1982.

McKinney H H, Mosaic diseases in the Canary Islands, West Africa and Gibraltar. *Journal of Agricultural Research* 39: 557–558, 1929.

Nagy J I and Maliga R, *Z. Pflanzenphysiologie* 78: 453–455, 1976.

Nitsch J P, Litsch C, *Science* 163: 85–87, 1969.

Paszkowski J, Shillito R D, Saul M, Mandak V, Hohn T, Hohn B, Potrykus I: Direct gene transfer to plants. *EMBO J* 3: 2717–2722, 1984.

Pennica D, et al., *Nature* 301: 214, 1983.

Pisan B, Potrykus I, Paszkowski J: Optimalization of turnip (*Brassica rapa*) protoplast culture of Cauliflower Mosaic Virus transformation. In: Potrytus I et al. (eds) Protoplast 1983, Poster Proceedings. Birkhauser Basel, 1983, 44–45.

Shillito R D et al., *Mutation Research* 81: 165–175, 1981.

Shillito R D, Paszkowski J, Potrykus I: Agarose plating and bead type culture technique enable and stimulate development of protoplast-derived colonies in number of plant species. Plant Cell Rep 2: 244–247, 1983.

Southern E M: Detection of specific sequences among DNA fragments separated by gel electrophoresis. *J. Mol Biol* 98: 503–517, 1975.

Stephien P, et al., *Gene* 24: 281–297, 1983.

Wienand U, et al., *Mol. Gen. Gent.,* 182: 440–444, 1981.

What is claimed is:

1. A process for the maintenance and proliferation of defective, non-infectious CaMV genomes in proliferating plant material, said CaMV genomes being unaccompanied by the T-DNA border regions of the Ti-plasmid, said process comprising:

culturing in a suitable nutrient medium proliferating isolated plant protoplasts, isolated plant cells or isolated plant tissues containing non-infectious CaMV genomes, said CaMV genomes being unaccompanied by the T-DNA border regions of the Ti-plasmid and being stably integrated into the plant genome, which CaMV genomes are not viable under natural conditions and have lost their ability to replicate in plant material.

2. A process according to claim 1, wherein the defective, non-infectious CaMV genomes are viral mutants selected from the group consisting of deletion mutants, substitution mutants, insertion mutants and mutants having rearranged viral genes.

3. A process according to claim 1, wherein the defective, non-infectious CaMV genomes are genetically modified containing non-viral genetic material heterologous with respect to the plant genome.

4. A process according to claim 1, which process comprises:

(a) isolating plant protoplasts;

(b) introducing a defective non-infectious CaMV genome into the genome of the plant protoplasts by incubation with polyethylene glycol; and (c) cultivating said protoplasts in a suitable nutrient medium.

5. A process according to claim 1, which process comprises:

(a) isolating plant protoplasts by treating appropriate plant material derived from leaves, stems, blossoms, roots, pollen, cotyledons, seedlings or seeds with suitable cellulase and pectinase enzymes;

(b) introducing a defective, non-infectious CaMV genome without the T-DNA border regions of the Ti-plasmid into said isolated plant protoplasts, by incubation with polyethylene glycol, while maintaining said plant protoplasts and the CaMV genome in a suitable incubation medium;

(c) cultivating said plant protoplasts containing the defective, non-infectious CaMV genome in a suitable nutrient medium in a temperature range from 7° C. to 42° C. and at a protoplast density of from 1 to $1\times10^6$ protoplasts/ml.

6. Proliferating isolated plant protoplasts, plant cells or plant tissues, which contain stably integrated into their genomes defective, non-infectious CaMV genomes.

7. Proliferating isolated plant protoplasts, plant cells or plant tissues according to claim 6, wherein the defective, non-infectious CaMV genomes are genetically modified CaMV genomes.

8. Proliferating isolated plant cells or plant tissues, which have been regenerated from plant protoplasts and plant cells, respectively, according to claim 6, which plant protoplasts or plant cells are derived from plants that are capable of being regenerated.

9. Proliferating isolated plant cells or plant tissues, which have been regenerated from plant protoplasts or plant cells, respectively, according to claim 7, which protoplasts or cells are derived from plants that are capable of being regenerated.

10. A process according to claim 1, which process comprises:

(a) isolating plant protoplasts by treating appropriate plant material derived from leaves, stems, blossoms, roots, pollen, cotyledons, seedlings or seeds with suitable cellulase and pectinase enzymes;

(b) introducing a defective, non-infectious CaMV genome, said CaMV genome being unaccompanied by the T-DNA border regions of the Ti-plasmid, into said isolated plant protoplasts by incubation with polyethylene glycol, while maintaining said plant protoplasts and the CaMV genome in a suitable incubation medium;

(c) transferring said plant protoplasts containing the defective, non-infectious CaMV genome into a suitable liquid nutrient medium, solidifying said medium with agarose, cutting the agarose-solidified medium into segments after setting, and transferring the segments to a suitable nutrient medium; and (d) cultivating said segments in a temperature range from 7° C. to 42° C.

* * * * *